United States Patent
Schnabel

(10) Patent No.: US 10,091,994 B2
(45) Date of Patent: Oct. 9, 2018

(54) FORMULATION ADDITIVES, PRODUCTION AND USE THEREOF

(71) Applicant: BAYER INTELLECTUAL PROPERTY GMBH, Monheim (DE)

(72) Inventor: Gerhard Schnabel, Elsenfeld (DE)

(73) Assignee: BAYER INTELLECTUAL PROPERTY GMBH, Monheim am Rhein (DE)

( * ) Notice: Subject to any disclaimer, the term of this patent is extended or adjusted under 35 U.S.C. 154(b) by 0 days.

(21) Appl. No.: 14/771,843

(22) PCT Filed: Mar. 5, 2014

(86) PCT No.: PCT/EP2014/054292
§ 371 (c)(1),
(2) Date: Sep. 1, 2015

(87) PCT Pub. No.: WO2014/135606
PCT Pub. Date: Sep. 12, 2014

(65) Prior Publication Data
US 2016/0015028 A1    Jan. 21, 2016

(30) Foreign Application Priority Data

Mar. 5, 2013 (DE) .................. 10 2013 003 655

(51) Int. Cl.
*A01N 25/30* (2006.01)
*A01N 57/20* (2006.01)

(52) U.S. Cl.
CPC .............. *A01N 25/30* (2013.01); *A01N 57/20* (2013.01)

(58) Field of Classification Search
CPC combination set(s) only.
See application file for complete search history.

(56) References Cited

U.S. PATENT DOCUMENTS

| 2,719,087 | A | * | 9/1955 | Knox, Jr. ............... G03C 1/043 430/636 |
| 3,775,349 | A | | 11/1973 | Tuvell et al. |
| 4,592,875 | A | | 6/1986 | Kesling et al. |
| 4,997,641 | A | | 3/1991 | Hartnett et al. |
| 5,846,905 | A | | 12/1998 | Frisch et al. |
| 6,008,181 | A | | 12/1999 | Cripe et al. |
| 2003/0087764 | A1 | | 5/2003 | Pallas et al. |
| 2005/0100562 | A1 | * | 5/2005 | Kurita .................. A01N 25/14 424/400 |
| 2007/0161512 | A1 | * | 7/2007 | Smith .................. A01N 25/04 504/207 |
| 2009/0318294 | A1 | * | 12/2009 | Malec .................. A01N 57/02 504/206 |

FOREIGN PATENT DOCUMENTS

| CA | 2388011 A1 | 2/2001 |
| DE | 4343856 A1 | 6/1995 |
| JP | 59193803 | * 11/1984 |
| JP | 2011105874 A | 6/2011 |
| WO | 0110211 A1 | 2/2001 |

OTHER PUBLICATIONS

Glyphosate Chemical Profile 2/85 (accessed on Feb. 3, 2018, pp. 1-5, http://pmep.cce.cornell.edu/profiles/herb-growthreg/fatty-alcohol-monuron/glyphosate/glyphos_prf_0285.html).*
Die Tenside, ed. Kurt Kosswig and Helmut Stache, Hanser 1993, pp. 130-133, as discussed on p. 2 of the subject application.
Die Tenside, ed. Kurt Kosswig and Helmut Stache, Hanser 1993, pp. 171-178, as discussed on p. 2 of the subject application.
International Search Report from corresponding PCT/EP2014/054292, dated Jun. 16, 2014.

* cited by examiner

*Primary Examiner* — Alma Pipic
(74) *Attorney, Agent, or Firm* — McBee Moore Woodward & Vanik IP, LLC

(57) ABSTRACT

The invention relates to novel formulation additives of formula 1 and to the production and use thereof, in particular as adjuvants and additives for agrochemical formulations. A novel combination of known ether sulfates and cations allows products with superior characteristics to be obtained, such as pesticides with improved strength.

15 Claims, No Drawings

FORMULATION ADDITIVES, PRODUCTION AND USE THEREOF

CROSS REFERENCE TO RELATED APPLICATIONS

This application is a § 371 National Stage Application of PCT/EP2014/054292, filed 5 Mar. 2014, which claims priority to DE 10 2013 003 655.0, filed 5 Mar. 2013.

BACKGROUND

Field of the Invention

The invention relates to the technical field of formulation, in particular the formulation of agrochemicals.

Description of Related Art

Plant protection compositions improved by compounds of the formula I.2 are based on the fact that the substances I.2 are novel surfactants having improved properties.

Agrochemical formulation technologies and the auxiliary substances necessary for these are well-known to the person skilled in the art. Recent research in these fields is often aimed at an increased action or an improved safety profile.

Thus e.g. sodium salts of sulfated $C_8$-$C_{18}$-alkanol ethoxylates are well-known as formulation auxiliaries. The alkyl chain of these surfactants can be branched or linear and of synthetic or natural origin. These surfactants are often employed as wetting agents or adjuvants, such as, for example, in the product Biopower of Bayer CS.

Although these surfactants can significantly increase the action of some active substances, a reduced action may occur with other active substances. The formulatability or gel formation may lead to massive problems with these surfactants, in particular in the process procedure of surfactant production or production of the formulation, and finally the result may be that the content of active substances and surfactants is relatively low.

The aim of the present invention was thus to discover novel surfactants which do not have these disadvantages.

It has been found, surprisingly, that certain salts of surfactants of the formula 1 completely or partially avoid the abovementioned disadvantages.

The present invention provides surfactants of the formula 1 and the production and use thereof as auxiliary substances in agrochemical formulations, wherein this also includes the use as adjuvants.

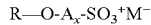 surfactants of the formula 1

DETAILED DESCRIPTION OF A PREFERRED EMBODIMENT

Surfactants of the formula 1 are novel. They can be produced by a procedure in which, for example, alcohols of the formula 2 are first alkoxylated. The resulting compounds of the formula 3 are known from the literature and for the most part are commercially obtainable. They are then converted into corresponding sulfates (eq. 1).

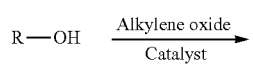

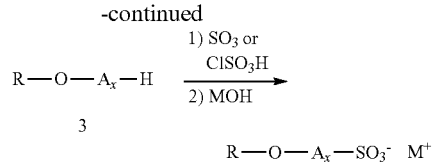

Alkoxylations and subsequent conversion into sulfates (anionic surfactants) by reaction with e.g. sulfur trioxide or Cl—SO$_3$H with subsequent neutralization are industrial chemical transformations for experts and as such are well-known. Suitable bases for the neutralization are e.g. KOH, choline hydroxide and hydroxides of the corresponding sulfur- or nitrogen-based cations. Alkoxylations, such as e.g. ethoxylation or propoxylation, are described in Die Tenside, ed. Kurt Kosswig and Helmut Stache, Hanser 1993, page 148 and the cited literature; sulfations are described in the same source on page 130 and the literature cited there.

Alternatively, surfactants of the formula 1 can be produced by a nucleophilic substitution according to equation 2 from an alcohol of the formula 2 and a sulfate of the formula 4.

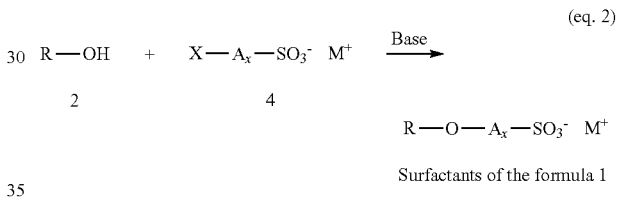

Surfactants of the formula 1 are characterized in that

R denotes an aliphatic ($C_8$-$C_{18}$) radical which can be linear or branched and saturated or mono- or polyunsaturated, A denotes a polyalkoxylene group which is composed of alkoxylene oxides, wherein the monomers can be different and the oligo- or polyalkoxylene unit are built up from the monomers blockwise or as a statistical mixture, M+ denotes a cation from the group of potassium, quaternary ammonium ion, sulfonium, phosphonium or sulfoxonium ion, X denotes a nuclefuge, such as, for example, Cl, Br, I or tosyl and x denotes a number between 1 and 100.

Preferred surfactants of the formula 1 are characterized in that

R denotes an aliphatic ($C_8$-$C_{16}$) radical which can be linear or branched and saturated or mono- or polyunsaturated, A denotes a polyalkoxylene group which is built up from ethylene oxide, propylene oxide and/or butylene oxide, wherein the monomers can be different and the oligo- or polyalkoxylene unit are built up from the monomers blockwise or as a statistical mixture, M denotes a cation from the group of potassium, quaternary (or quaternized) ammonium ion which contains no nitrogen-hydrogen bond, sulfonium, phosphonium or sulfoxonium ion, in particular potassium and quaternary (or quaternized) ammonium which contains no nitrogen-hydrogen bond and x denotes a number between 1 and 20.

Particularly preferred surfactants of the formula 1 are characterized in that

R denotes an aliphatic ($C_8$-$C_{14}$) radical which can be linear or branched and saturated or mono- or polyunsaturated, A denotes a polyalkoxylene group which is built up from ethylene oxide, propylene oxide and/or butylene oxide, wherein the monomers can be different and the oligo- or polyalkoxylene unit are built up from the monomers blockwise or as a statistical mixture, M denotes a cation from the group of potassium or quaternary (or quaternized) ammonium ion which contains no nitrogen-hydrogen bond and x denotes a number between 1 and 10.

Surfactants of the formula 1 surprisingly show advantages which known and in some cases commercially available surfactants do not have. For example, the surfactants of the formula 1 are an adjuvant for agorchemical active substances or plant protection compositions which is better in many cases. Although the surfactants of structure 1 generally have advantageous properties, preferred embodiments can be revealed by controlled variation of the individual structural elements.

A preferred embodiment is characterized in that the radical R is a mixture of $C_{12}$ and $C_{14}$ radicals.

A further preferred embodiment is characterized in that the radical R is an isotridecyl radical ($^iC_{13}$ radical).

A further preferred embodiment is characterized in that the radical R is a 2-ethylhexyl radical.

A further preferred embodiment is characterized in that the radical R is a 2-propylheptyl radical.

A further preferred embodiment is characterized in that the alkoxylate block A is a polymeric or oligomeric unit which is built up from the monomers ethylene oxide, propylene oxide and butylene oxide under base catalysis, wherein the linkage between the various monomers can be blockwise or as a statistical mixture.

A further preferred embodiment is characterized in that the alkoxylate block A is a polymeric or oligomeric unit which is built up blockwise from the units ethylenoxy (EO), propylenoxy (PO) and butylenoxy (BO) in accordance with the following equation:

$$A=(BO)s(PO)u(EO)z(PO)w(BO)v$$

In this:
EO denotes ethylenoxy unit (ethoxylene unit): —$CH_2$—$CH_2$—O—
PO denotes proylenoxy unit (propoxylene unit): —$CH_2$—CHMe-O— or —CHMe-$CH_2$—O—
BO denotes butylenoxy unit (butoxylene unit): —$CH_2$—CHEt-O or —CHEt-$CH_2$—O— or —CHMe-CHMe-O—, preferably —$CH_2$—CHEt-O or —CHEt-$CH_2$—O—
Me denotes methyl
Et denotes ethyl
s denotes 0-100, preferably 0-10, in particular 0-5
u denotes 0-100, preferably 0-10, in particular 0-5
z denotes 0-100, preferably 1-50, in particular 1.5-20, particularly 1.7 to 10
w denotes 0-50, preferably 0-10, in particular 0-5
v denotes 0-50, preferably 0-10, in particular 0-5
x denotes 1.

A further preferred embodiment is characterized in that the alkoxylate block A is a polyethoxylene unit —($CH_2$—$CH_2$—O)$_z$. 

A further preferred embodiment is characterized in that "z" is a number between 0.5 and 10, preferably a number between 1.5 and 4.5.

A further preferred embodiment is characterized in that the cation M is the potassium cation.

A further preferred embodiment is characterized in that the cation M is a quaternized ammonium ion, such as, for example, $Me_3N$—$CH_2$—$CH_2$—OH, $NMe_4$, $NEt_4$, $NPr_4$ and $NBu_4$.

Surfactants of the formula 1 can be used as formulation aids for plant protection compositions or as adjuvants. Both uses are likewise novel and are included in this application If surfactants of the formula 1 are obtained in liquid form or as solid, free-flowing products, these can be used directly as formulation auxiliaries or adjuvants.

As a rule surfactants of the formula 1 are combined with at least one further auxiliary substance to give a solid, paste-like or liquid mixture.

Adjuvants according to the invention are preferably characterized in that they comprise
at least one surfactant of the formula 1,
and
at least one further formulation aid.

The use of the surfactants of the formula 1 as a formulation auxiliary, such as e.g. as a wetting agent, is characterized in that an agrochemical formulation comprises between 0.1 percent by weight and 80 percent by weight of one or more surfactants of the formula 1.

The use as an adjuvant is characterized in that as a rule between 20 g and 1,000 g of surfactant 1 or a mixture of surfactants of the formula 1 are applied per one hectare. Surfactants of the formula 1 can also be mixed with further adjuvants which are not according to the invention.

If surfactants of the formula 1 are employed as an adjuvants for agrochemicals, such as e.g. pesticides, these can be employed as an "adjuvant" without an active substance, or they can be formulated together with one or more agrochemical active substances, so that the corresponding plant protection compositions already include an adjuvant.

If surfactants of the formula 1 are used as adjuvants which are formulated together with one or more agrochemical active substances, both solid and liquid formulations are suitable.

When adjuvants based on surfactants of the formula 1 are prepared, these are as a rule liquid formulations which as a rule are distinguished by a highest possible content of surfactant or surfactants of the formula 1. In such cases further surfactants and further auxiliary substances can be present in the formulation.

The production and use of surfactants 1 as adjuvants is a further preferred embodiment. In particular liquid adjuvants having a content of 5 percent by weight, preferably of at least 10 percent by weight and very particularly of at least 20 percent by weight of surfactant(s) 1 are a preferred embodiment.

The production and use of plant protection compositions which comprise one or more surfactants 1 are likewise novel and the subject matter of this invention.

Plant protection compositions according to the invention are characterized in that they comprise
at least one surfactant of the formula 1
at least one pesticide (agrochemical active substance)
at least one further formulation auxiliary
and
optionally further agrochemicals.

Preferred plant protection compositions according to the invention are characterized in that they comprise
have at least 15 percent by weight of one or more surfactants of the formula 1 at least one leaf-active agrochemical active substance
optionally one or more further pesticides (agrochemical active substances)
at least one further formulation auxiliary
and
optionally further agrochemicals.

Surfactants of the formula 1 are as a rule incorporated into suitable formulations before these are used. Adjuvants, formulation auxiliaries, formulation methods and technologies such as are used e.g. in agrochemical formulations are well-known to the person skilled in the art and are described e.g. in Proceedings from Formulation Forum '97, Formulation Science, Vol 1 (Chester L. Foy, David W. Pritchard, George B. Beestman); Chemistry and Technology of Agrochemical Formulations (ISBN 0-7514-0443-8; publisher: D. A. Knowles, Kluwer Academic Publishers 1998; Formulierungstechnik (Hans Mollet, Arnold Grubenmann; Wiley-VCH Verlag GmbH, 2000); and literature cited there.

Suitable formulations which comprise one or more surfactants 1 according to the invention are solid and liquid formulations. These formulations can be single- or multiphase. In the case of liquid formulations these can be aqueous or non-aqueous solutions, oil-in-water or water-in-oil (micro)emulsions, suspensions, capsule suspensions, suspoemulsions or mixed forms of these formulations. In the case of solid formulations these can be e.g. dusts, powders, granules or compacted forms, such as tablets.

Suitable formulation auxiliaries are e.g. solvents, stabilizers, such as pH stabilizers (buffers, acids, bases), antioxidants and UV stabilizers, surfactants, such as emulsifiers, dispersing agents or wetting agents, coloring agents, such as dyestuffs or pigments, thickeners, in particular thickeners which impart thixotropic properties to a liquid mixture, polymers which e.g. increase the viscosity of a solution, increase the adhesion of a solution or increase the solubility of active substances in a liquid phase (solubilizers), or which combine several of the properties mentioned, defoamers, adsorptive carriers, absorptive carriers, biocides, such as e.g. fungicides or bactericides, auxiliary substances for improving resistance to rain, release or flow agents, antidrift agents, corrosion inhibitors, propellants, such as dimethyl ether, butane, propane, carbon dioxide, nitrogen or mixtures of various propellants, such as butane and propane.

Preferred formulation auxiliaries are organic solvents, water, thickeners, stabilizers, antioxidants, surfactants, biocides, dyestuffs, pigments and combinations thereof.

Suitable solvents are organic solvents and water.

Suitable organic solvents of the formulations according to the invention are selected from saturated, mono- or polyunsaturated, cyclic or acyclic, branched or unbranched, unsubstituted or mono- or polysubstituted hydrocarbons, including aromatic and heteroaromatic compounds and combinations thereof.

Suitable organic solvents are unsubstituted or mono- or polysubstituted, wherein the substituents are one or more representatives from the following group: oxo, oxy, hydroxy, carboxy, carboxamido, alkoxy, alkoxycarbonyl, carbamoyl, amino, imido, imino, thioyl, sulfonyl, sulfinyl, sulfo, sulfanyl, disulfanyl, ether group, ester group, keto group, aldehyde group, acetal group, carbonate group, nitrile group, sulfide group, sulfoxide group, sulfone group or halogen selected from fluorine, chlorine, bromine, iodine.

Preferred organic solvents are aliphatic (C1-C18)-alcohols, wherein the aliphatic radical can be linear or branched or also cyclic and saturated or unsaturated, e.g. methanol, ethanol, isopropanol, n-propanol, butanol, pentanol, 1-, 2- or 3-hexanol, allyl alcohol, amyl alcohol, glycol, propylene glycol, glycerol or sugar syrup. Preferred organic solvents and/or dispersing agents are furthermore aromatic alcohols, such as e.g. benzyl alcohol or 4-methoxybenzyl alcohol.

Preferred organic solvents are furthermore ether compounds, such as e.g. tertiary butyl methyl ether, diethyl ether, anisole, alkoxylates, such as polyglycols, polyalkoxylated alcohols and polyglycerols.

Preferred organic solvents are furthermore esters, such as e.g. ethyl acetate, isopropyl acetate, propyl acetate, butyl acetate, C8-C18-fatty acid methyl esters, C8-C18-fatty acid ethyl esters, substituted or unsubstituted benzoic acid esters, such as e.g. benzoic acid methyl ester, benzoic acid ethyl ester, p-methoxybenzoic acid methyl ester.

Preferred organic solvents are furthermore aldehydes, such as e.g. hexanal, decanal, benzaldehyde, 4-methoxybenzaldehyde.

Preferred organic solvents are furthermore ketones, such as e.g. cyclohexanone, 4-methoxyacetophenone, acetophenone, acetone, butanone (methyl ethyl ketone).

Preferred organic solvents are furthermore nitriles, such as e.g. acetonitrile, benzonitrile.

Preferred organic solvents are furthermore amides, such as e.g. N-octylpyrrolidone, octanoic acid dimethylamide, decanecarboxylic acid dimethylamide or dodecanoic acid dimethylamide.

Preferred organic solvents are furthermore acetals, such as e.g. benzaldehyde dimethyl acetal, 4-methoxybenzaldehyde dimethyl acetal, benzaldehyde diethyl acetal.

Preferred organic solvents are furthermore orthoesters, such as, for example, 1,1,1-triethoxyethane.

Preferred organic solvents are furthermore sulfones and sulfoxides, such as e.g. dimethyl sulfone, sulfolane, dimethylsulfoxide.

Preferred organic solvents are furthermore carbonates, such as e.g. propylene carbonate, glycerol carbonate.

The content of suitable organic solvents or water in formulations according to the invention can be up to 95 percent by weight, preferably up to 75 percent by weight, in particular up to 50 percent by weight.

Examples of UV absorbers are inorganic UV absorbers, such as e.g. titanium dioxide, zinc dioxide, and organic UV absorbers, such as e.g. compounds which are commercially obtainable under the brand name Uvinul, e.g. benzophenone-9, diethylamino hydroxybenzoyl hexyl benzoate, ethylhexyltriazone, oxybenzone, octyl methoxycinnamate, octocrylene, polyethylene glycol-25 4-aminobenzoic acid, benzophenone-4 and combinations thereof. The content of UV absorbers can be up to 100,000 ppm.

Examples of antioxidants are tocopherols (vitamin E), such as e.g. D,L-alpha-tocopherol, ascorbic acid, t-butylhydroquinones (TBHQ), butylated hydroxytoluenes and butylated hydroxyanisoles. The content of antioxidants in the bait composition according to the invention is up to 100,000 ppm.

Examples of surfactants are salts, such as alkali metal, alkaline earth metal or ammonium salts of ligninsulfonic acids, naphthalenesulfonic acids, phenolsulfonic acids, dibutylnaphthalenesulfonic acids, alkylarylsulfonic acids, alkyl sulfates, alkylsulfonates, fatty alcohol sulfates, sulfated fatty alcohol glycol ethers, furthermore condensation products of sulfonated naphthalene or naphthalene products and formaldehyde, condensation products of naphthalene or naphthalenesulfonic acid with phenol and formaldehyde, tributylphenyl polyglycol ethers, such as e.g. compounds which are marketed as Sapogenats by Clariant, nonionic surfactants, such as e.g. tristerylphenyl polyglycol ethers, such as e.g. compounds which are marketed as Soprophors by Rhodia, fatty alcohol alkoxylates, such as e.g. ethylene oxide consates, castor oil ethoxylates, alkyl polyglycosides, e.g. alkyl polyglucosides, polymeric surfactants, such as e.g. block copolymers of the type EO-PO, EO-PO-EO or PO-EO-PO, wherein EO denotes blocks from the monomer ethylene oxide and PO denotes blocks from the monomer propylene oxide. Instead of propylene oxide, butylene oxide can also be employed.

In surfactants the terminal OH group of (alkyl)glycol units can be further modified by standard reactions. Sulfation or phosphation gives acid surfactants, which can be partially or completely neutralized. The resulting salts—e.g. alkali metal or ammonium salts—are likewise suitable surfactants. Alkylation, such as methylation, or acylation, e.g. acetylation, gives neutral surfactants having closed end groups.

Preferred nonionic surfactants are alkyl polyglyycosides and fatty acid alkoxylates, such as e.g.: Lutensol XP 30, Lutensol TO 6, Lutensol TO 8, Lutensol TO 10, Lutensol TO 15, Genapol X-060, Genapol X-080, Genapol X-150. The terminal OH groups of these surfactants can also be closed, e.g. by a methyl group. Examples of alkyl polyglucosides are Lutensol GD 70, Agnique PG 8105-G, Agnique PG 8107-G. The surfactants of the brands Lutensol and Agnique are commercially obtainable from BASF AG, surfactants of the brand Genapol are commercially obtainable from Clariant AG.

The content of surfactants in formulations according to the invention can be up to 50 percent by weight, preferably up to 30 percent by weight and in particular up to 15 percent by weight.

Examples of defoamers are silicone defoamers, such as e.g. silicone emulsions (suitable compounds are marketed e.g. under the brand names Silikon® SRE of Wacker or Rhodorsil® of Rhodia), long-chain alcohols or fatty acids, which can also be alkoxylated, in particular propoxylated.

The content of defoamers in formulations according to the invention can be up to 5 percent by weight, preferably up to 3 percent by weight.

Examples of thickeners (i.e. auxiliary substances which impart to the product pseudo-plastic flow properties, i.e. impart to the fluid a high viscosity in the resting state and a low viscosity in the agitated state) are, for example, polysaccharides or organically modified minerals or laminar silicates, such as e.g. xanthan gum (e.g. Kelzan® from Kelco), Rhodopol® 23 (Rhone-Poulenc) or Veegum® (from R.T. Vanderbilt) or Attaclay® (from Engelhardt) or bentonites or Byk D-410 or Byk D-420.

The content of thickeners in formulations according to the invention can be up to 5 percent by weight, preferably up to 3 percent by weight.

Suitable coloring agents are, for example, pigments and dyestuffs. Both pigments which are poorly soluble in water and dyestuffs which are soluble in solvents, such as e.g. water, can be used. Examples are the compounds obtainable under the following brand names: Rhodamin B, C.I. Pigment Red 112 and C.I. Solvent Red 1 and Pigment Blue 15:4, Pigment Blue 15:3, Pigment Blue 15:2, Pigment Blue 15:1, Pigment Blue 80, Pigment Yellow 1, Pigment Yellow 13, Pigment Red 112, Pigment Red 48:2, Pigment Red 48:1, Pigment Red 57:1, Pigment Red 53:1, Pigment Orange 43, Pigment Orange 34, Pigment Orange 5, Pigment Green 36, Pigment Green 7, Pigment White 6, Pigment Brown 25, Basic Violet 10, Basic Violet 49, Acid Red 51, Acid Red 52, Acid Red 14, Acid Blue 9, Acid Yellow 23, Basic Red 10, Basic Red 108 and dyestuffs thereof, such as e.g. Disperse Blue 69-0007. These products are commercially obtainable.

The content of coloring agents in formulations according to the invention can be up to five percent by weight, preferably up to one percent by weight.

Examples of suitable absorptive carriers are Sipernat 50 or Sipernat 50S.

The content of carriers in formulations according to the invention can be up to 50 percent by weight, preferably up to 30 percent by weight.

Examples of bactericides are Proxel® from ICI, Acticide® RS from Thor Chemie, Kathon® MK from Rohm & Haas and Dowicil® from Dow Elanco.

The content of bactericides in formulations according to the invention can be up to five percent by weight, preferably up to one percent by weight.

Examples of flow agents are minerals, such a kaolin and alumosilicates.

The content of flow agents in formulations according to the invention can be up to 50 percent by weight, preferably up to 30 percent by weight.

Examples of auxiliary substances for improving the resistance to rain are tallow, paraffin waxes and plant waxes, such as beeswax or carnauba wax.

The content of auxiliary substances for improving the resistance to rain in formulations according to the invention can be up to 50 percent by weight, preferably up to 30 percent by weight.

Preferred formulation auxiliaries are organic solvents, water, biocides, surfactants, defoamers, thickeners, dyestuffs, pigments and combinations thereof.

The content of preferred formulation auxiliaries in formulations according to the invention can be up to 95 percent by weight, preferably up to 75 percent by weight, in particular up to 50 percent by weight.

One or more agrochemical active substances can optionally be present in the formulations according to the invention, such as e.g. be herbicides, safeners, fungicides, insecticides, molluscicides, nematicides, plant growth regulators, rodenticides. These are well-known and are described in The Pesticide Manual, 16th edition (British Crop Protection Council). Particularly preferred substances are herbicides, such as glyphosate and salts thereof, in particular mono- and dipotassium salts and the isopropylammonium salt, ALS inhibitors, such as sulfonylureas and salts thereof, such as nicosulfuron, foramsulfuron, mesosulfuron, iodosulfuron, metsulfuron or rimsulfuron, ACCase inhibitors, such as e.g. fenoxaprop-p-ethyl, glufosinate and salts thereof, HPPD inhibitors, such as e.g. sulcotrione, IFT or mesotrione, and safeners, such as, for example, isoxadiphen-ethyl or mefenpyr-diethyl.

The content of agrochemical active substances in formulations according to the invention can be up to 85 percent by weight, preferably up to 70 percent by weight, in particular up to 50 percent by weight.

Further agrochemicals which the formulations according to the invention can optionally comprise are e.g.: adjuvants, such as wetting agents, penetration promoters, such as Mero or Hasten, humectants, such as e.g. glycerol, fertilizers, such as e.g. ammonium sulfate, ammonium nitrate, potassium nitrate, ammonium phosphate, potassium salts of phosphoric acid, potassium chloride, potassium sulfate, potassium carbonate or urea.

The content of further agrochemicals in formulations according to the invention can be up to 85 percent by weight, preferably up to 50 percent by weight.

The surfactants 1 according to the invention are conventionally converted into suitable formulations so that these are easy to use. Suitable formulations are liquid and solid formulations.

Preferred formulations are, particularly, aqueous formulations, in particular those in which surfactants of the formula 1 are present in dissolved form, such as e.g. solutions. Very particularly preferred formulations are liquid formulations which have a content of at least 50 g of compound 1 per liter, preferably of at least 100 g of surfactant 1' per liter, and in particular of at least 200 g of surfactant 1 per liter. Solutions according to the invention are easily accessible by stirring and dissolving surfactants 1 according to the invention in a suitable solvent, such as, for example, water, at room temperature. Further auxiliary substances can additionally be added, such as biocides or other surfactants. Further agrochemical active substances which can be added to aqueous formulations are e.g. glyphosate and salts thereof, in particular the mono- and dipotassium and the isopropyl salts.

Solid formulations can be prepared by, for example, absorbing surfactants 1 according to the invention on a suitable carrier, such as e.g. Sipernat 50 S, and grinding the carrier with a suitable dispersing agent and flow agent, e.g. by means of an air jet mill. The resulting powder can then be used directly as a powder for preparing spray liquors, but it can also be made into a paste with a little water and converted into granules by means of extrusion. The content of surfactants 1 according to the invention in solid formulations is preferably at least 5 percent by weight, particularly preferably at least 10 percent by weight.

Agrochemical formulations of the compounds 1 can be applied directly, in particular sprayed, on to target organisms, such as e.g. harmful plants, on to plant crops or target areas. They can be diluted beforehand with a suitable carrier, such as e.g. water or organic solvents, and then applied or sprayed. A preferred carrier is water.

For uses, as a rule the required application amounts per hectare are diluted with water to a volume of 5 l to 5,000 l, preferably to a volume of 50 l to 2,000 l. In addition further products important to agronomists can be added to the spray liquor, such as e.g. further plant protection compositions, adjuvants, additives for preparing spray liquors, such as e.g. defoamers, fertilizers or trace minerals.

Plant protection compositions as a rule comprise chemical active substances which either are prepared by synthesis or are active substances of natural origin, or "biologicals", i.e. plant protection compositions which are approved in ecological agriculture. An overview of these plant protection compositions is to be found in The Pesticide Manual, 16th edition (British Crop Protection Council) and The BioPesticide Manual, 15th edition.

Preferred plant protection compositions are herbicides, fungicides, insecticides, accaricides, nematicides, plant growth regulators, safeners and rodenticides, in particular herbicides and safeners.

The method of controlling harmful organisms by application of agrochemical formulations which comprise compounds of the formula 1 is likewise novel and the subject matter of this invention. In particular, the active substance formulations according to the invention with the surfactants 1 according to the invention and formulations thereof are suitable for controlling harmful organisms in crops of useful plants which are not genetically modified, such as e.g. conventional maize, cereals, such as oats, rye, rice, wheat, barley, triticale or dinkel. In addition, however, the active substances 1 according to the invention and formulations thereof are also suitable for controlling harmful organisms in genetically modified plant crops, e.g. in insecticide- or herbicide-resistant useful plant or ornamental plant crops. Methods of controlling harmful organisms in plant crops which have a genetically produced resistance to one or more active substances, such as glyphosate, glufosinate, ALS inhibitors, HPPD inhibitors, or towards auxins, such as 2,4-D or dicamba, are particularly preferred.

Combinations of leaf-active agrochemical active substances (i.e. active substances which display their action when they are applied to green parts of plants) and surfactants of the formula 1 are very particularly preferred and are a preferred embodiment. Examples of leaf-active pesticides are glyphosate and salts derived therefrom (e.g. mono-, di- or tri-salts with the cations K, $NH_4$, $^iPrNH_3$)

glufosinate and salts derived therefrom (e.g. mono- or di-salts with the cations $NH_4$, and K)

auxins (natural and synthetic) and salts derived therefrom, such as e.g. dicamba, 2,4-D, ALS inhibitors, such as sulfonylureas and salts derived therefrom, such as e.g. metsulfuron, mesosufuron, nicosulfuron, foramsulfuron, and HPPD inhibitors, such as e.g. triketones, such as sulcotrione, mesotrione and salts derived therefrom.

Particularly preferred plant protection compositions according to the invention are characterized in that they comprise at least 15 percent by weight of one or more surfactants of the formula 1 at least 15 percent by weight of one or more leaf-active agrochemical active substances (pesticides)

at least one further formulation auxiliary and optionally further agrochemicals.

The following list of combinations of surfactants 1 with herbicides and/or surfactants or adjuvants or tank mix additives illustrate the scope of the present invention. These combinations are novel and likewise the subject matter of this invention. In this list "+" stands for "combined with". If the active substances mentioned are acids, these can be employed in the form of the free acid or salts thereof. The potassium salts and ammonium salts are preferred in this context, in particular the potassium and quaternized ammonium ion, wherein no proton is bonded to the nitrogen.

1) Surfactant 1+glyphosate
2) Surfactant 1+glufosinate
3) Surfactant 1+glyphosate+glufosinate
4) Surfactant 1+sulfonylureas, such as nicosulfuron, rimsulfuron, mesosulfuron, iodosulfuron or foramsulfuron
5) Surfactant 1+auxin, such as e.g. 2,4-D or dicamba
6) Surfactant 1+glyphosate+dicamba
7) Surfactant 1+glyphosate+2,4-D
8) Surfactant 1+HPPD inhibitors, such as e.g. sulcotrione, mesotrione or IFT
9) Surfactant 1+alkyl polyglycosides, such as e.g. alkyl polyglucosides
10) Surfactant 1+fatty alcohol ethoxylates, such as isotridecyloxy ethoxylates
11) Surfactant 1+fatty acids or salts thereof
12) Surfactant 1+ammonium sulfate
13) Surfactant 1+ammonium sulfate+glyphosate
14) Surfactant 1+ammonium sulfate+alkyl polyglucoside+glyphosate
15) Surfactant 1+ammonium sulfate+glufosinate 16) Surfactant 1+ammonium sulfate+alkyl polyglucoside+glufosinate
17) Surfactant 1+ammonium sulfate+alkyl polyglucoside+glyphosate+glufosinate
18) Surfactant 1+ammonium sulfate+alkyl polyglucoside+glyphosate+2,4-D
19) Surfactant 1+ammonium sulfate+alkyl polyglucoside+glyphosate+dicamba
20) Surfactant 1+potassium carbonate
21) Surfactant 1+potassium carbonate+glyphosate
22) Surfactant 1+potassium carbonate+alkyl polyglucoside+glyphosate
23) Surfactant 1+potassium carbonate+glufosinate
24) Surfactant 1+potassium carbonate+alkyl polyglucoside+glufosinate
25) Surfactant 1+potassium carbonate+alkyl polyglucoside+glyphosate+glufosinate
26) Surfactant 1+potassium carbonate+alkyl polyglucoside+glyphosate+2,4-D
27) Surfactant 1+potassium carbonate+alkyl polyglucoside+glyphosate+dicamba
28) Surfactant 1+potassium carbonate+glycerol+glyphosate
29) Surfactant 1+potassium carbonate+glycerol+alkyl polyglucoside+glyphosate
30) Surfactant 1+potassium carbonate+glycerol+glufosinate
31) Surfactant 1+potassium carbonate+glycerol+alkyl polyglucoside+glufosinate
32) Surfactant 1+potassium carbonate+glycerol+alkyl polyglucoside+glyphosate+glufosinate
33) Surfactant 1+potassium carbonate+glycerol+alkyl polyglucoside+glyphosate+2,4-D
34) Surfactant 1+potassium carbonate+glycerol+alkyl polyglucoside+glyphosate+dicamba
35) Surfactant 1.1+glyphosate
36) Surfactant 1.1+glufosinate
37) Surfactant 1.1+glufosinate+glyphosate
38) Surfactant 1.1+nicosulfuron
39) Surfactant 1.1+rimsulfuron
40) Surfactant 1.1+mesosulfuron
41) Surfactant 1.1+iodosulfuron
42) Surfactant 1.1+foramsulfuron
43) Surfactant 1.1+2,4-D
44) Surfactant 1.1+dicamba
45) Surfactant 1.1+glyphosate+dicamba
46) Surfactant 1.1+glyphosate+2,4-D
47) Surfactant 1.1+sulcotrione
48) Surfactant 1.1+mesotrione
49) Surfactant 1.1+IFT
50) Surfactant 1.1+Agnique PG 8105-G
51) Surfactant 1.1+Agnique PG 8107-G
52) Surfactant 1.1+Lutensol GD 70
53) Surfactant 1.1+Lutensol TO 5
54) Surfactant 1.1+Lutensol TO 8
55) Surfactant 1.1+Lutensol TO 10
56) Surfactant 1.1+Lutensol TO 15
57) Surfactant 1.1+Lutensol XP 3
58) Surfactant 1.1+Lutensol XP 5
59) Surfactant 1.1+coconut fatty acid
60) Surfactant 1.1+tallow fatty acid
61) Surfactant 1.1+dodecanoic acid
62) Surfactant 1.1+ammonium sulfate
63) Surfactant 1.1+ammonium sulfate+glyphosate
64) Surfactant 1.1+ammonium sulfate+Agnique PG 8107-G+glyphosate
65) Surfactant 1.1+ammonium sulfate+glufosinate
66) Surfactant 1.1+ammonium sulfate+Agnique PG 8107-G+glufosinate
67) Surfactant 1.1+ammonium sulfate+Agnique PG 8107-G+glyphosate+glufosinate
68) Surfactant 1.1+ammonium sulfate+Agnique PG 8107-G+glyphosate+2,4-D
69) Surfactant 1.1+ammonium sulfate+Agnique PG 8107-G+glufosinate+dicamba
70) Surfactant 1.1+potassium carbonate
71) Surfactant 1.1+potassium carbonate+glyphosate potassium salt
72) Surfactant 1.1+potassium carbonate+Agnique PG 8107-G+glyphosate kalim salt
73) Surfactant 1.1+potassium carbonate+glufosinate
74) Surfactant 1.1+potassium carbonate+Agnique PG 8107-G+glufosinate
75) Surfactant 1.1+potassium carbonate+Agnique PG 8107-G+glyphosate+glufosinate
76) Surfactant 1.1+potassium carbonate+Agnique PG 8107-G+glyphosate+2,4-D
77) Surfactant 1.1+potassium carbonate+Agnique PG 8107-G+glyphosate+dicamba
78) Surfactant 1.1+potassium carbonate+glycerol+glyphosate
79) Surfactant 1.1+potassium carbonate+glycerol+Agnique PG 8107-G+glyphosate
80) Surfactant 1.1+potassium carbonate+glycerol+glufosinate
81) Surfactant 1.1+potassium carbonate+glycerol+Agnique PG 8107-G+glufosinate
82) Surfactant 1.1+potassium carbonate+glycerol+Agnique PG 8107-G+glyphosate+glufosinate
83) Surfactant 1.1+potassium carbonate+glycerol+Agnique PG 8107-G+glyphosate+2,4-D
84) Surfactant 1.1+potassium carbonate+glycerol+Agnique PG 8107-G+glyphosate+dicamba
85) Surfactant 1.3+glyphosate
86) Surfactant 1.3+glufosinate
87) Surfactant 1.3+glyphosate+glufosinate
88) Surfactant 1.3+nicosulfuron
89) Surfactant 1.3+rimsulfuron
90) Surfactant 1.3+mesosulfuron
91) Surfactant 1.3+iodosulfuron
92) Surfactant 1.3+foramsulfuron
93) Surfactant 1.3+2,4-D
94) Surfactant 1.3+dicamba
95) Surfactant 1.3+glyphosate+dicamba
96) Surfactant 1.3+glyphosate+2,4-D
97) Surfactant 1.3+sulcotrione,
98) Surfactant 1.3+mesotrione
99) Surfactant 1.3+IFT
100) Surfactant 1.3+Agnique PG 8105-G
101) Surfactant 1.3+Agnique PG 8107-G
102) Surfactant 1.3+Lutensol GD 70
103) Surfactant 1.3+Lutensol TO 5
104) Surfactant 1.3+Lutensol TO 8
105) Surfactant 1.3+Lutensol TO 10
106) Surfactant 1.3+Lutensol TO 15
107) Surfactant 1.3+Lutensol XP 3
108) Surfactant 1.3+Lutensol XP 5
109) Surfactant 1.3+coconut fatty acid
110) Surfactant 1.3+tallow fatty acid
111) Surfactant 1.3+dodecanoic acid
112) Surfactant 1.3+ammonium sulfate
113) Surfactant 1.3+ammonium sulfate+glyphosate
114) Surfactant 1.3+ammonium sulfate+Agnique PG 8107-G+glyphosate 115) Surfactant 1.3+ammonium sulfate+glufosinate
116) Surfactant 1.3+ammonium sulfate+Agnique PG 8107-G+glufosinate
117) Surfactant 1.3+ammonium sulfate+Agnique PG 8107-G+glyphosate+glufosinate
118) Surfactant 1.3+ammonium sulfate+Agnique PG 8107-G+glyphosate+2,4-D
119) Surfactant 1.3+ammonium sulfate+Agnique PG 8107-G+glyphosate+dicamba
120) Surfactant 1.3+potassium carbonate
121) Surfactant 1.3+potassium carbonate+glyphosate
122) Surfactant 1.3+potassium carbonate+Agnique PG 8107-G+glyphosate
123) Surfactant 1.3+potassium carbonate+glufosinate
124) Surfactant 1.3+potassium carbonate+Agnique PG 8107-G+glufosinate
125) Surfactant 1.3+potassium carbonate+Agnique PG 8107-G+glyphosate+glufosinate
126) Surfactant 1.3+potassium carbonate+Agnique PG 8107-G+glyphosate+2,4-D
127) Surfactant 1.3+potassium carbonate+Agnique PG 8107-G+glyphosate+dicamba
128) Surfactant 1.3+potassium carbonate+glycerol+glyphosate
129) Surfactant 1.3+potassium carbonate+glycerol+Agnique PG 8107-G+glyphosate–
130) Surfactant 1.3+potassium carbonate+glycerol+glufosinate
131) Surfactant 1.3+potassium carbonate+glycerol+Agnique PG 8107-G+glufosinate
132) Surfactant 1.3+potassium carbonate+glycerol+Agnique PG 8107-G+glyphosate+glufosinate
133) Surfactant 1.3+potassium carbonate+glycerol+Agnique PG 8107-G+glyphosate+2,4-D
134) Surfactant 1.3+potassium carbonate+glycerol+Agnique PG 8107-G+glufosinate+dicamba
135) Surfactant 1.1+mesosulfuron+mefenpyr-diethyl
136) Surfactant 1.1+iodosulfuron+mefenpyrdiethyl
137) Surfactant 1.1+foramsulfuron+isoxadiphen-ethyl

EXAMPLES

Experiment 1 According to the Invention 100 g of a mixture of saturated, linear $C_{12}$- and $C_{14}$-alcohols are initially introduced into a high-grade steel autoclave and 0.5% NaOH is added. Water is then stripped off at temperatures of from 130° C. to 180° C. 2 molar equivalents of ethylene oxide are then added and the reaction is carried out to give the corresponding fatty alcohol ethoxylate 3.1. The resulting product is reacted with $ClSO_3H$ (1.1 molar equivalents), while cooling. When the reaction has ended air is passed through the apparatus in order to remove hydrogen chloride. The resulting acid is slowly neutralized with dilute potassium hydroxide solution (2 N), while cooling. All the volatile components are then stripped off under a high vacuum. The residue can either be purified further (e.g. by a silica gel filtration with a polar, anhydrous solvent system, such as e.g. tetrahydrofuran, ethyl acetate or ethanol, and subsequent stripping off of the solvent under a high vacuum) or be employed directly in adjuvant studies or formulation experiments. Surfactant 1.1 can be prepared in this manner with a purity of at least 90%.

The surfactants of the formula 1 of Table 1 can be prepared in an analogous manner. Ammonium salts, in particular quaternized ammonium salts, of the formula 1 are accessible by employing a dilute hydroxide solution of the corresponding ammonium ion for neutralization of the acid intermediately formed instead of KOH.

TABLE 1

Surfactants of the formula 1 according to the invention

| Surfactant | R-O— | A $(BO)_s(PO)_u(EO)_z$ $(PO)_w(BO)_v$ | s | u | z | w | v | M+ |
|---|---|---|---|---|---|---|---|---|
| 1.1 | $C_{12}$-/$C_{14}$-alkyl-O— | —(EO)z— | 0 | 0 | 2 | 0 | 0 | K |
| 1.2 | $C_{12}$-/$C_{14}$-alkyl-O— | —(EO)z— | 0 | 0 | 2 | 0 | 0 | $Me_3NCH_2CH_2OH$ |
| 1.3 | $C_{12}$-/$C_{14}$-alkyl-O— | —(EO)z— | 0 | 0 | 2.5 | 0 | 0 | K |
| 1.4 | $C_{12}$-/$C_{14}$-alkyl-O— | —(EO)z— | 0 | 0 | 3.2 | 0 | 0 | K |
| 1.5 | $C_{12}$-/$C_{14}$-alkyl-O— | —(EO)z— | 0 | 0 | 5 | 0 | 0 | K |
| 1.6 | isotridecyl-O— | —(EO)z— | 0 | 0 | 1.8 | 0 | 0 | $Me_3NCH_2CH_2OH$ |
| 1.7 | isotridecyl-O— | —(EO)z— | 0 | 0 | 2.5 | 0 | 0 | $Me_3NCH_2CH_2OH$ |
| 1.8 | isotridecyl-O— | —(EO)z— | 0 | 0 | 3.5 | 0 | 0 | $Me_3NCH_2CH_2OH$ |
| 1.9 | isotridecyl-O— | —(EO)z— | 0 | 0 | 10 | 0 | 0 | $NMe_4$ |
| 1.10 | 2-ethyl-hexyl-O— | —(PO)u(EO)z— | 0 | 1.5 | 4 | 0 | 0 | K |
| 1.11 | 2-ethyl-hexyl-O— | —(PO)u(EO)z— | 0 | 1.5 | 6 | 0 | 0 | K |
| 1.12 | 2-ethyl-hexyl-O— | —(PO)u(EO)z— | 0 | 1.5 | 8 | 0 | 0 | K |
| 1.13 | 2-ethyl-hexyl-O— | —(PO)u(EO)z— | 0 | 1.5 | 10 | 0 | 0 | K |
| 1.14 | 2-ethyl-hexyl-O— | —(PO)u(EO)z (PO)w— | 0 | 1.5 | 4.5 | 1 | 0 | K |
| 1.15 | 2-ethyl-hexyl-O— | —(EO)z(PO)w— | 0 | 0 | 4 | 1.5 | 0 | K |

TABLE 1-continued

Surfactants of the formula 1 according to the invention

| Surfactant | R-O— | A $(BO)_s(PO)_u(EO)_z(PO)_w(BO)_v$ | s | u | z | w | v | M+ |
|---|---|---|---|---|---|---|---|---|
| 1.16 | 2-ethyl-hexyl-O— | —(EO)z(PO)w— | 0 | 0 | 6 | 1.5 | 0 | K |
| 1.17 | 2-ethyl-hexyl-O— | —(EO)z(PO)w— | 0 | 0 | 8 | 1.5 | 0 | K |
| 1.18 | 2-ethyl-hexyl-O— | —(EO)z(BO)v | 0 | 0 | 6 | 0 | 1 | K |
| 1.19 | 2-propyl-heptyl-O— | —(PO)u(EO)z— | 0 | 1.5 | 4 | 0 | 0 | K |
| 1.20 | 2-propyl-heptyl-O | —(PO)u(EO)z— | 0 | 1.5 | 6 | 0 | 0 | K |
| 1.21 | 2-propyl-heptyl-O | —(PO)u(EO)z— | 0 | 1.5 | 8 | 0 | 0 | K |
| 1.22 | 2-propyl-heptyl-O | —(PO)u(EO)z— | 0 | 1.5 | 10 | 0 | 0 | K |
| 1.23 | 2-propyl-heptyl-O | —(PO)u(EO)z(PO)w— | 0 | 1.5 | 4.5 | 1 | 0 | K |
| 1.24 | 2-propyl-heptyl-O | —(EO)z(PO)w— | 0 | 0 | 4 | 1.5 | 0 | K |
| 1.25 | 2-propyl-heptyl-O | —(EO)z(PO)w— | 0 | 0 | 6 | 1.5 | 0 | K |
| 1.26 | 2-propyl-heptyl-O | —(EO)z(PO)w— | 0 | 0 | 8 | 1.5 | 0 | K |
| 1.27 | 2-propyl-heptyl-O | —(EO)z(BO)v | 0 | 0 | 6 | 0 | 1 | K |
| 1.28 | $C_{12}$-alkyl-O— | —(PO)u(EO)z— | 0 | 1.5 | 4 | 0 | 0 | K |
| 1.29 | $C_{12}$-alkyl-O— | —(PO)u(EO)z— | 0 | 1.5 | 6 | 0 | 0 | K |
| 1.30 | $C_{12}$-alkyl-O— | —(PO)u(EO)z— | 0 | 1.5 | 8 | 0 | 0 | K |
| 1.31 | $C_{12}$-alkyl-O— | —(PO)u(EO)z— | 0 | 1.5 | 10 | 0 | 0 | K |
| 1.32 | $C_{12}$-alkyl-O— | —(PO)u(EO)z(PO)w— | 0 | 1.5 | 4.5 | 1 | 0 | K |
| 1.33 | $C_{12}$-alkyl-O— | —(EO)z(PO)w— | 0 | 0 | 4 | 1.5 | 0 | K |
| 1.34 | $C_{12}$-alkyl-O— | —(EO)z(PO)w— | 0 | 0 | 6 | 1.5 | 0 | K |
| 1.35 | $C_{12}$-alkyl-O— | —(EO)z(PO)w— | 0 | 0 | 8 | 1.5 | 0 | K |
| 1.36 | $C_{12}$-alkyl-O— | —(EO)z(BO)v | 0 | 0 | 6 | 0 | 1 | K |
| 1.37 | isotridecyl-O— | —(PO)u(EO)z— | 0 | 1.5 | 4 | 0 | 0 | K |
| 1.38 | isotridecyl-O— | —(PO)u(EO)z— | 0 | 1.5 | 6 | 0 | 0 | K |
| 1.39 | isotridecyl-O— | —(PO)u(EO)z— | 0 | 1.5 | 8 | 0 | 0 | K |
| 1.40 | isotridecyl-O— | —(PO)u(EO)z— | 0 | 1.5 | 10 | 0 | 0 | K |
| 1.41 | isotridecyl-O— | —(PO)u(EO)z(PO)w— | 0 | 1.5 | 4.5 | 1 | 0 | K |
| 1.42 | isotridecyl-O— | —(EO)z(PO)w— | 0 | 0 | 4 | 1.5 | 0 | K |
| 1.43 | isotridecyl-O— | —(EO)z(PO)w— | 0 | 0 | 6 | 1.5 | 0 | K |
| 1.44 | isotridecyl-O— | —(EO)z(PO)w— | 0 | 0 | 8 | 1.5 | 0 | K |
| 1.45 | isotridecyl-O— | —(EO)z(BO)v— | 0 | 0 | 6 | 0 | 1 | K |
| 1.46 | $C_{14}$-/$C_{16}$-alkyl-O— | —(PO)u(EO)z— | 0 | 1.5 | 4 | 0 | 0 | K |
| 1.47 | $C_{14}$-/$C_{16}$-alkyl-O— | —(PO)u(EO)z— | 0 | 1.5 | 6 | 0 | 0 | K |
| 1.48 | $C_{14}$-/$C_{16}$-alkyl-O— | —(PO)u(EO)z— | 0 | 1.5 | 8 | 0 | 0 | K |
| 1.49 | $C_{14}$-/$C_{16}$-alkyl-O— | —(PO)u(EO)z— | 0 | 1.5 | 10 | 0 | 0 | K |
| 1.50 | $C_{14}$-/$C_{16}$-alkyl-O— | —(PO)u(EO)z(PO)w— | 0 | 1.5 | 4.5 | 1 | 0 | K |
| 1.51 | $C_{14}$-/$C_{16}$-alkyl-O— | —(EO)z(PO)w— | 0 | 0 | 4 | 1.5 | 0 | K |
| 1.52 | $C_{14}$-/$C_{16}$-alkyl-O— | —(EO)z(PO)w— | 0 | 0 | 6 | 1.5 | 0 | K |
| 1.53 | $C_{14}$-/$C_{16}$-alkyl-O— | —(EO)z(PO)w— | 0 | 0 | 8 | 1.5 | 0 | K |
| 1.54 | $C_{14}$-/$C_{16}$-alkyl-O— | —(EO)z(BO)v— | 0 | 0 | 6 | 0 | 1 | K |
| 1.55 | 2-ethyl-hexyl-O— | —(PO)u(EO)z(PO)w(BO)v— | 0 | 2.5 | 8 | 1 | 2 | K |
| 1.56 | 2-ethyl-hexyl-O— | —(PO)u(EO)z(BO)v— | 0 | 2.5 | 8 | 0 | 2 | K |

TABLE 1-continued

Surfactants of the formula 1 according to the invention

| Surfactant | R-O— | A $(BO)_s(PO)_u(EO)_z$ $(PO)_w(BO)_v$ | s | u | z | w | v | M+ |
|---|---|---|---|---|---|---|---|---|
| 1.57 | 2-ethyl-hexyl-O— | —(EO)z— | 0 | 0 | 1.5 | 0 | 0 | K |
| 1.58 | 2-ethyl-hexyl-O— | —(EO)z— | 0 | 0 | 2 | 0 | 0 | NMe$_4$ |
| 1.59 | 2-ethyl-hexyl-O— | —(EO)z— | 0 | 0 | 2.5 | 0 | 0 | K |
| 1.60 | 2-propyl-heptyl-O— | —(EO)z— | 0 | 0 | 1.5 | 0 | 0 | K |
| 1.61 | 2-propyl-heptyl-O— | —(EO)z | 0 | 0 | 2 | 0 | 0 | NMe$_4$ |
| 1.62 | 2-propyl-heptyl-O— | —(EO)z— | 0 | 0 | 2.5 | 0 | 0 | K |
| 1.63 | C$_{12}$-alkyl-O— | —(EO)z— | 0 | 0 | 1.5 | 0 | 0 | K |
| 1.64 | C$_{12}$-alkyl-O— | —(EO)z— | 0 | 0 | 2 | 0 | 0 | NMe$_4$ |
| 1.65 | C$_{12}$-alkyl-O— | —(EO)z— | 0 | 0 | 2.5 | 0 | 0 | K |
| 1.66 | C$_{14}$-/C$_{16}$-alkyl-O— | —(EO)z— | 0 | 0 | 1.5 | 0 | 0 | K |
| 1.67 | C14-/C$_{16}$-alkyl-O— | —(EO)z— | 0 | 0 | 2 | 0 | 0 | NMe$_4$ |
| 1.68 | C14-/C$_{16}$-alkyl-O— | —(EO)z— | 0 | 0 | 2.5 | 0 | 0 | K |
| 1.69 | C$_{16}$-alkyl-O— | —(EO)z— | 0 | 0 | 2.5 | 0 | 0 | K |
| 1.70 | C$_{16}$-alkyl-O— | —(EO)z— | 0 | 0 | 4.5 | 0 | 0 | K |
| 1.71 | C$_{18}$-alkyl-O— | —(EO)z— | 0 | 0 | 2.5 | 0 | 0 | K |
| 1.72 | C$_{18}$-alkyl-O— | —(EO)z— | 0 | 0 | 4.5 | 0 | 0 | K |
| 1.73 | C$_{12}$-alkyl-O— | —(BO)$_s$(EO)$_z$ | 1 | 0 | 3 | 0 | 0 | K |
| 1.74 | C$_{12}$-/C$_{14}$-alkyl-O | —(BO)$_s$(EO)$_z$ (PO)$_w$(BO)$_v$- | 2 | 0 | 8 | 0 | 0 | K |

The abbreviations in Table 1 have the following meanings:
C12-alkyl-O— dodecyloxy
isotridecyl-O— isotridecyloxy
C14-/C16-alkyl-O— mixture of tetradecyloxy and hexadecyloxy
C12-/C14-alkyl-O— mixture of dodecyloxy and tetradecyloxy
2-ethylhexyl-O— 2-ethylhexyloxy
2-propylheptyl-O— 2-propylheptyloxy

Experiment 2 According to the Invention 10 g of surfactant 1.1 (purity >90%) are dissolved together with 0.1 g of Acticide MBS (bactericide; Thor-Chemie) in 39.9 g of water. Depending on the purity of surfactant 1.1, an elevated temperature and intensive thorough mixing may be necessary for this. An adjuvant which comprises surfactant 1.1 in an amount of 20 percent by weight and can be employed directly for biological tests is obtained in this way.

Experiment 3 According to the Invention 10 g of surfactant 1.1 are suspended with 30 g of glyphosate (acid) in 30 g of water, and 2 molar equivalents of pulverulent potassium hydroxide (2 molar equivalents with respect to glyphosate) are added, while cooling. The mixture is then topped up with water to a weight of 100 g.

An adjuvant-containing glyphosate formulation which comprises surfactant 1.1 is obtained in this way. This formulation can be used directly for biological tests.

Biological Comparative Experiment

In a greenhouse experiment wheat is grown as a model plant for undesirable plant growth. After the young plants have reached a growth height of approx. 20 cm they are treated with glyphosate (Touchdown HiTech from Syngenta, dipotassium salt of glyphosate, without adjuvant) and an adjuvant.

In an experiment according to the invention 150 g/ha—converted—of glyphosate (as Touchdown HiTech) are mixed with 300 g/ha of surfactant 1.1 (corresponds to 1.5 kg of adjuvant according to the invention from Experiment 1 according to the invention) and water to give a spray liquor of 400 l/ha and the mixture is applied to wheat plants approx. 20 cm high.

In a corresponding comparative experiment 150 g/ha—converted—of glyphosate (as Touchdown HiTech) are mixed with 300 g/ha of a comparable anionic surfactant with sodium as the cation (in the form of Genapol LRO: 28%) and water to give a spray liquor of 400 l/ha and the mixture is likewise applied to wheat plants approx. 20 cm high.

The two experiments are evaluated by measuring the height of green parts of the plants 2 weeks after the application.

It is seen, surprisingly, that the adjuvant according to the invention with surfactant 1.1 is significantly superior in adjuvant action to the surfactant Genapol LRO.

The invention relates to the following subject matter
Surfactants of the formula 1

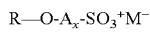   (surfactants of the formula 1)

wherein
R denotes an aliphatic (C$_8$-C$_{18}$) radical which can be linear or branched and saturated or mono- or polyunsaturated,
A denotes a polyalkoxylene group which is composed of alkoxylene oxides, wherein the monomers can be different and the oligo- or polyalkoxylene unit are built up from the monomers blockwise or as a statistical mixture, M denotes a cation from the group of potassium, quaternary ammonium ion, sulfonium, phosphonium or sulfoxonium ion, and x denotes a number between 1 and 100.

Surfactants of the formula 1, wherein

R denotes an aliphatic ($C_8$-$C_{16}$) radical which can be linear or branched and saturated or mono- or polyunsaturated, A denotes a polyalkoxylene group which is built up from ethylene oxide, propylene oxide and/or butylene oxide, wherein the monomers can be different and the oligo- or polyalkoxylene unit are built up from the monomers blockwise or as a statistical mixture, M denotes a cation from the group of potassium, quaternary (or quaternized) ammonium ion which contains no nitrogen-hydrogen bond and x denotes a number between 1 and 20, preferably between 1 and 10.

Surfactants of the formula 1, wherein the alkoxylate block A is a polymeric or oligomeric unit which is built up blockwise from the units ethylenoxy (EO), propylenoxy (PO) and butylenoxy (BO) in accordance with the following equation:

$$A=(BO)s(PO)u(EO)z(PO)w(BO)v$$

and wherein

EO denotes ethylenoxy unit (ethoxylene unit): —$CH_2$—$CH_2$—O—

PO denotes propylenoxy unit (propoxylene unit): —$CH_2$—CHMe-O— or —CHMe-$CH_2$—O—

BO denotes butylenoxy unit (butoxylene unit): —$CH_2$—CHEt-O or —CHEt-$CH_2$—O— or —CHMe-CHMe-O—, preferably —$CH_2$—CHEt-O or —CHEt-$CH_2$—O—

Me denotes methyl

Et denotes ethyl s denotes 0-100, preferably 0-10, in particular 0-5 u denotes 0-100, preferably 0-10, in particular 0-5 z denotes 0-100, preferably 1-50, in particular 1.5-20, particularly 1.7 to 10 w denotes 0-50, preferably 0-10, in particular 0-5 and v denotes 0-50, preferably 0-10, in particular 0-5 and x denotes 1.

Surfactants of the formula 1, wherein

R corresponds to an aliphatic radical from the group 2-etyhlhexyl; 2-propylhexyl; a mixture of n-dodecyl and n-tetradecyl; n-dodecyl; isotridecyl; a mixture of n-tetradecyl and n-hexadecyl; or n-hexadecyl.

Surfactants of the formula 1, wherein the polyalkoxylene block A is built up from two different alkoxylene radicals, wherein one alkoxylene radical is an ethoxylene radical.

Surfactants of the formula 1, wherein the polyalkoxylene block A is built up from only one alkoxylene radicals, wherein it is preferably the ethoxylene and the propoxylene radical, preferably the ethoxylene radical.

Production of the surfactants of the formula 1, wherein alcohols of the formula 2 are converted into the compounds 3 which are then neutralized to give the surfactants 1.

Use of surfactants of the formula 1 or surfactants produced in a method as described above as a formulation auxiliary.

Use of surfactants of the formula 1 or surfactants produced in a method as described above as an adjuvant for agrochemical products, such as pesticides.

Liquid or solid formulations comprising or consisting of at least one surfactant of the formula 1 or at least one surfactant produced in a method described above for use as auxiliary substances or as adjuvants, wherein they comprise
at least one surfactant of the formula 1,
and optionally
at least one further auxiliary.

Liquid or solid formulations with surfactants of the formula 1, wherein the content of one or more surfactants of the formula 1 is at least 5 percent by weight, preferably 10 percent by weight and in particular 20 percent by weight.

Liquid formulations, preferably solutions, with surfactants of the formula 1, wherein the content of one or more surfactants of the formula 1 is at least 5 percent by weight, preferably 10 percent by weight and in particular 20 percent by weight.

Production of formulations as described above, in particular with surfactants of the formula 1 or at least one surfactant produced in a method as described above, wherein at least one surfactant of the formula 1 is combined with at least one formulation auxiliary which is not according to the invention and optionally further components.

Liquid and solid agrochemical formulations or plant protection compositions, comprising or consisting of
at least one surfactant of the formula 1,
at least one pesticide
optionally further agrochemicals
and
at least one further formulation auxiliary.

Liquid and solid plant protection compositions, wherein the agrochemical formulations comprise one or more leaf-active active substances from the group:
glyphosate and salts derived therefrom (e.g. mono-, di- or tri-salts with the cations K, $NH_4$, $^iPrNH_3$)
glufosinate and salts derived therefrom (e.g. mono- or di-salts with the cations $NH_4$, and K)
natural or synthetic auxin and salts derived therefrom, such as e.g. dicamba, 2,4-D
ALS inhibitors, such as sulfonylureas and salts derived therefrom, such as e.g. metsulfuron, mesosufuron, nicosulfuron, iodosulfuron or foramsulfuron, and/or
HPPD inhibitors, such as e.g. triketones, such as sulcotrione, mesotrione and salts derived therefrom.

Plant protection compositions or agrochemical formulations which comprise
at least 15 percent by weight of one or more surfactants of the formula 1
at least 15 percent by weight of one or more leaf-active agrochemical active substances
at least one further formulation auxiliary
and
optionally further agrochemicals.

Production of plant protection compositions or agrochemical formulations, wherein a composition as described above and wherein at least one surfactant of the formula 1, a pesticide and a formulation auxiliary which is not according to the invention and optionally further components are combined with one another.

Use of agrochemical plant protection compositions as described above or plant protection compositions or agrochemical formulations produced in a method as described above for controlling harmful organisms.

The invention claimed is:

1. A liquid agrochemical formulation or plant protection composition in the form of an aqueous or non-aqueous solution comprising (a) at least 15 percent by weight of the formulation or composition of one or more surfactants of formula 1, $$R\text{—}O\text{-}A_x\text{-}SO_3^-M^+ \qquad (1)$$

wherein

R denotes an aliphatic radical which is n-dodecyl, n-tetradecyl, isotridecyl, or n-hexadecyl;

A denotes a polyalkoxylene group which is built up from ethoxylene and/or propoxylene radicals and which has the formula $$(BO)s(PO)u(EO)z(PO)w(BO)v$$

in which

BO denotes a butenyloxy unit,
PO denotes a propylenoxy unit,
EO denotes an ethylenoxy unit,
s denotes 0,
u denotes 0 to 10,
z denotes 1 to 50,
w denotes 0 to 10, and
v denotes 0,
M denotes a potassium cation, and
x denotes 1, (b) at least 15 per cent by weight of at least one herbicide which is a leaf-active active substance selected from the group consisting of glyphosate, salts derived from glyphosate, glufosinate, and salts derived from glufosinate, (c) optionally one or more further agrochemicals, and (d) at least one further formulation auxiliary, wherein at least one formulation auxiliary is selected from the group consisting of an organic solvent and water and forms an aqueous or non-aqueous solution of the formulation or composition.

2. The liquid agrochemical formulation or plant protection composition as claimed in claim 1, wherein the content of one or more surfactants of formula 1 is at least 20 percent by weight by weight of the formulation or composition.

3. The liquid agrochemical formulation or plant protection composition as claimed in claim 1, wherein the agrochemical formulation or plant protection composition comprises one or more leaf-active active substances selected from the group consisting of glyphosate,
mono-, di- and tri-salts derived from glyphosate with the cations K, $NH_4$ or $^iPrNH_3$, glufosinate, and
mono- and di-salts derived from glufosinate with the cations $NH_4$ or K.

4. The liquid agrochemical formulation or plant protection composition as claimed in claim 1, wherein R is n-dodecyl,
A denotes a polyalkoxylene group which is built up from ethylene oxide, and
M is potassium.

5. The liquid agrochemical formulation or plant protection composition as claimed in claim 1, wherein A denotes a polyalkoxylene block built up from only ethoxylene radicals.

6. The liquid agrochemical formulation or plant protection composition as claimed in claim 1 comprising a mixture of the surfactants, comprising surfactants wherein R is n-dodecyl and comprising surfactants where R is n-tetradecyl.

7. The liquid agrochemical formulation or plant protection composition as claimed in claim 1 wherein the agrochemical formulation or plant protection composition comprises glyphosate.

8. The liquid agrochemical formulation or plant protection composition as claimed in claim 1 wherein the agrochemical formulation or plant protection composition comprises mono-, di- and tri-salts derived from glyphosate with the cations K, $NH_4$ or $^iPrNH_3$.

9. The liquid agrochemical formulation or plant protection composition as claimed in claim 1 wherein the agrochemical formulation or plant protection composition comprises glufosinate.

10. The liquid agrochemical formulation or plant protection composition as claimed in claim 1 wherein the agrochemical formulation or plant protection composition comprises mono- and di-salts derived from glufosinate with the cations $NH_4$ or K.

11. The liquid agrochemical formulation or plant protection composition as claimed in claim 1 wherein u denotes 0 to 1.5, z denotes 1.8 to 10, w denotes 0 to 1.5.

12. The liquid agrochemical formulation or plant protection composition as claimed in claim 1 wherein u denotes 0, z denotes 1.8 to 10, and w denotes 0.

13. The liquid agrochemical formulation or plant protection composition as claimed in claim 1 wherein the formulation auxiliary comprises water.

14. A method for production of plant protection composition or agrochemical formulation comprising a liquid agrochemical formulation or plant protection composition as claimed in claim 1, said method comprising combining at least one surfactant of formula 1, an herbicide selected from the group consisting of glyphosate, a salt derived from glyphosate, glufosinate, and a salt derived from glufosinate, and a formulation auxiliary and optionally one or more further components.

15. A method for controlling one or more organisms comprising applying a liquid agrochemical formulation or plant protection composition according to claim 1 to the one or more organisms or a target area.

* * * * *